(12) United States Patent
Dukic et al.

(10) Patent No.: US 8,318,230 B2
(45) Date of Patent: Nov. 27, 2012

(54) USE OF DEBRANCHED STARCH IN EXTRUSION-SPHERONIZATION PHARMACEUTICAL PELLETS

(75) Inventors: Aleksandra Dukic, Krnjaca-Beograd (YU); Chris Vervaet, Izegem (BE); Jean Paul Remon, Melle (BE); Paul A. Altieri, Skillman, NJ (US); Paul B. Foreman, Somerville, NJ (US)

(73) Assignees: Henkel AG & Co. KGaA, Duesseldorf (DE); Universiteit Gent, Ghent (BE)

( * ) Notice: Subject to any disclaimer, the term of this patent is extended or adjusted under 35 U.S.C. 154(b) by 1094 days.

(21) Appl. No.: 11/410,375

(22) Filed: Apr. 25, 2006

(65) Prior Publication Data

US 2006/0246192 A1 Nov. 2, 2006

Related U.S. Application Data

(60) Provisional application No. 60/677,182, filed on May 2, 2005.

(51) Int. Cl.
*A23B 4/03* (2006.01)
(52) U.S. Cl. .................................................... 426/454
(58) Field of Classification Search .................. None
See application file for complete search history.

(56) References Cited

U.S. PATENT DOCUMENTS

| | | | | | |
|---|---|---|---|---|---|
| 5,049,394 A | * | 9/1991 | Howard et al. | ............... | 424/490 |
| 5,281,276 A | * | 1/1994 | Chiu et al. | ...................... | 127/65 |
| 5,350,584 A | * | 9/1994 | McClelland et al. | ......... | 424/501 |
| 5,725,676 A | | 3/1998 | Chiu et al. | | |
| 5,830,884 A | * | 11/1998 | Kasica et al. | ................. | 514/160 |
| 6,054,302 A | | 4/2000 | Shi et al. | | |
| 2007/0075453 A1 | * | 4/2007 | Ayats et al. | .................. | 264/140 |

FOREIGN PATENT DOCUMENTS

| EP | 0512249 | 11/1992 |
|---|---|---|
| EP | 0499648 B1 | 12/1993 |
| WO | WO99/09066 | 2/1999 |

OTHER PUBLICATIONS

Basit et al., Formulation of Ranitidine Pellets by Extrusion-Spheronization with Little or No Microcrystalline Cellulose, 1999, Pharma Devel Training, 4(4), 499-505.*

Gu, et al., "Wet Spheronization by Rotary Processing-A Multistate Single-Pot Process for Producing Spheroids," Drug Dev. Ind. Pharm. 30(2):111-123 (2004).
Pisek, et al., "Comparison of Direct Rotor Pelletization (Fluid Bed) and High-Shear Pelletization Method for Pellet Production," Pharm. Ind. 67(2) 243-248 (2005).
Gainotti, et al., "Drug-B-Cyclodextrin Containing Pellets Prepared with a High-Shear Mixer," Drug Dev. Ind. Pharm. 30(10): 1061-1068 (2004).
Perissutti, et al., "Formulation Design of Carbamazepine Fast-Release Tablets Prepared by Melt Granulation Technique," Int. J. Pharm. 256: 53-63 (2003).
Sienkiewicz, et al., "Spheronization of Theophylline-Avicel Combinations Using a Fluid-Bed Rotogranulation Technique," Drug Dev. Ind. Pharm. 23(2): 173-182 (1997).
Vervaet, et al., "Extrusion-Spheronization: A Literature Review," Int. J. Pharm. 116: 131-146 (1995).
Prieto, et al., "Starch-Dextrin Mixtures as Base Excipients for Extrusion-Spheronization Pellets," Euro. J. Pharm. Biopharm. XX: 1-11 (2004).
Zhou, et al., "Matrix Pellets Based onthe Combination of Waxes, Starches and Maltodextrins," Int. J. Pharm. 133: 155-160 (1996).
Zhou, et al., "Optimization of the Processing of Matrix Pellets Based on the Combination of Waxes and Starch Using Exper. Design," Drug. Dev. Ind. Pharm. 24(4): 353-358(1998).
Zhou, et al., "Influence of Processing on the Characteristics of Matrix Pellets Based on Microcrystalline Waxes and Starch Derivatives," Int. J. Pharm. 146: 23-30 (1997).
Zhou, et al., "Bioavailability of Ibuprofen from Matrix Pellets Based on the Combination of Waxes and Starch Derivatives," Int. J. Pharm. 168: 79-84 (1998).
Junnila, et al., "Effects of Surface Active Agent on the Size, Shape and Hardness of Microcrystalline Cellulose/Maize Starch . . . ," S.T.P. Pharma Sciences 8(4) 221-226 (1998).
Handbook of Pharm.I Granulation Tech, ed. Parikh, Marcel Dekker: New York, Ch 11, pp. 333-368—O'Connor, et al., Pheronization I. Am-J. Pharm. Jul.-Sep., pp. 80-87 (1984).
Junnila, et al., "Waxy Corn Starch: A Potent Cofiller in Pellets Production Produced by Extrusion Spheronization," Pharm. Dev. Tech. 5(1): 67-76 (2000).
Bao, Jiahan et al. Rhelogical and mechanical properties of materials suited for extrusion-spheronization. Journal of Anhui University of Technology. Jan. 2004. vol. 1, Issue 1, p. 21.
O'Conner, Robert E. et al. "Spheronization I: Processing and Evaluation of Spheres Prepared from Commercially Available Exipients." American Journal of Pharmacy, Jul.-Sep. 1984, pp. 80-87.

* cited by examiner

*Primary Examiner* — Suzanne Ziska

(74) *Attorney, Agent, or Firm* — Sun Hee Lehmann

(57) ABSTRACT

This patent pertains to the use of debranched starch in the preparation of pharmaceutical pellets by extrusion spheronization. Such excipients are useful in any dry dosage form, including tablets and capsules, for either immediate or sustained release.

24 Claims, 2 Drawing Sheets

Figure 1. In-vitro drug release profiles of pellets containing Starch 1a, Starch 2a, and Avicel PH 101.

USE OF DEBRANCHED STARCH IN EXTRUSION-SPHERONIZATION PHARMACEUTICAL PELLETS

This application claims priority to provisional application U.S. Ser. No. 60/677,182 filed May 2, 2005.

BACKGROUND OF THE INVENTION

The present invention relates to the use of debranched starch in the preparation of pharmaceutical pellets by extrusion-spheronization.

Extrusion-spheronization is a process well-known in the art of pharmaceuticals, to prepare spheres for pharmaceutical uses, including both conventional and controlled release dosage forms. The process is based on the following steps:
 a) mixing at least one debranched starch and a liquid to form a moistened plastically deformable mass;
 b) extruding the mass to obtain an extrudate;
 c) spheronizing the extrudate to obtain a plurality of substantially spherical pellets; and
 d) drying of the pellets.

Such dosage forms may also optionally consist of several inert materials, referred to as excipients, in addition to the active ingredient, which is present in amounts sufficient to accomplish the desired pharmaceutical effect. These excipients are generally classified according to their functions, such as fillers (also called bulking agents and diluents), binders which hold the ingredients together, binder-fillers which perform both functions and disintegrants which help the dosage form to break apart and release the active ingredient when placed in a fluid environment.

Conventionally, extrusion-spheronization uses microcrystalline cellulose as the primary pharmaceutical excipient. However, microcrystalline cellulose is expensive and also is inadequate for use with certain active ingredients. Furthermore, since microcrystalline cellulose-based pellets do not disintegrate in gastrointestinal fluids, the release of less soluble active ingredients is prolonged. Due to these limitations, there is a need for microcrystalline cellulose replacement for use in pellet production.

Alternative excipients have been tried in the art, primarily cellulose derivatives, as well as blends. However, it has been difficult to find a replacement for microcrystalline cellulose as the primary excipient in extrusion-spheronization. Many of the alternatives tried have failed in such regards as difficult to extrude or spheronize, poor water absorption or retention within the extrudate, low quality size and shape distribution, and/or poor dissolution and release of the active agent.

Corn starch, wheat starch and waxy corn starch have been tried in extrusion-spheronization and determined to be unsatisfactory due to inadequate consistency and the fact that water is not homogeneously distributed, resulting in poor spheronization and inadequate pellets.

Surprisingly, it has now been discovered that crystalline, debranched starches provide an excellent replacement for microcrystalline cellulose in extrusion spheronization, and have excellent characteristics and properties.

SUMMARY OF THE INVENTION

This patent pertains to the use of crystalline debranched starch in the preparation of pharmaceutical pellets by extrusion-spheronization. Such excipients are useful in any dry dosage form, including tablets and capsules, for either immediate or sustained release.

The starch excipients can be used as a total replacement for microcrystalline cellulose or can be used as a partial replacement in combination with microcrystalline cellulose and/or other cellulose derivatives.

The term pellet, as used herein, is a substantially spherical solid particle whose diameter size may range from about 100 microns to about 3 mm.

As used herein, the term dosage form is intended in its broadest sense to mean not only pharmaceutical dosage forms which employ excipients to deliver active agent(s) and includes tablets (such as immediate release, sustained release, controlled release, modified release, and effervescent), capsules, pellets, and granules, but also non-pharmaceutical forms of these products.

Excipient, as used herein includes binders, fillers, and all other ingredients which are pharmacologically inert.

As used herein, the term debranched starch, refers to any starch which has been enzymatically hydrolyzed by at least one enzyme capable of cleaving the 1,6-linkages of the starch molecule.

As used herein, the term waxy or low amylose starch is intended to include a starch containing less than 10% amylose by weight of the dry starch.

As used herein, the term amylose-containing starch is intended to include any starch containing at least 10% amylose by weight of the dry starch.

As used herein, the term high amylose is intended to include a starch containing at least 50% amylose by weight of the dry starch.

Gelatinization, as used herein, is intended to mean the process by which starch is cooked out and loses its granular structure. Granular is intended to mean the structure of native starch in which the starch is not water soluble (still at least partly crystalline) and has birefringence and typically a Maltese cross under polarized light. In high amylose starches, some native granules do not exhibit a Maltese cross, particularly filamentous granules. During gelatinization, as used herein, starch loses its birefringent property as well as any Maltese cross present in its native state.

Pellet aspect ratio is intended to mean the ratio of the largest and the smallest diameter of a pellet. In one embodiment, the aspect ratio is about 1.

Friability is intended to mean the tendency of the pellets to flake off during handling resulting in the formation of dust.

Crystalline starch is intended to mean a starch that is crystalline, either due to its granular nature or because the gelatinized starch is allowed to recrystalline by methods known in the art. The crystalline property of starch may be evidenced by x-ray diffraction as shown in Example 6 of the examples section.

DETAILED DESCRIPTION OF THE INVENTION

Figure 1:
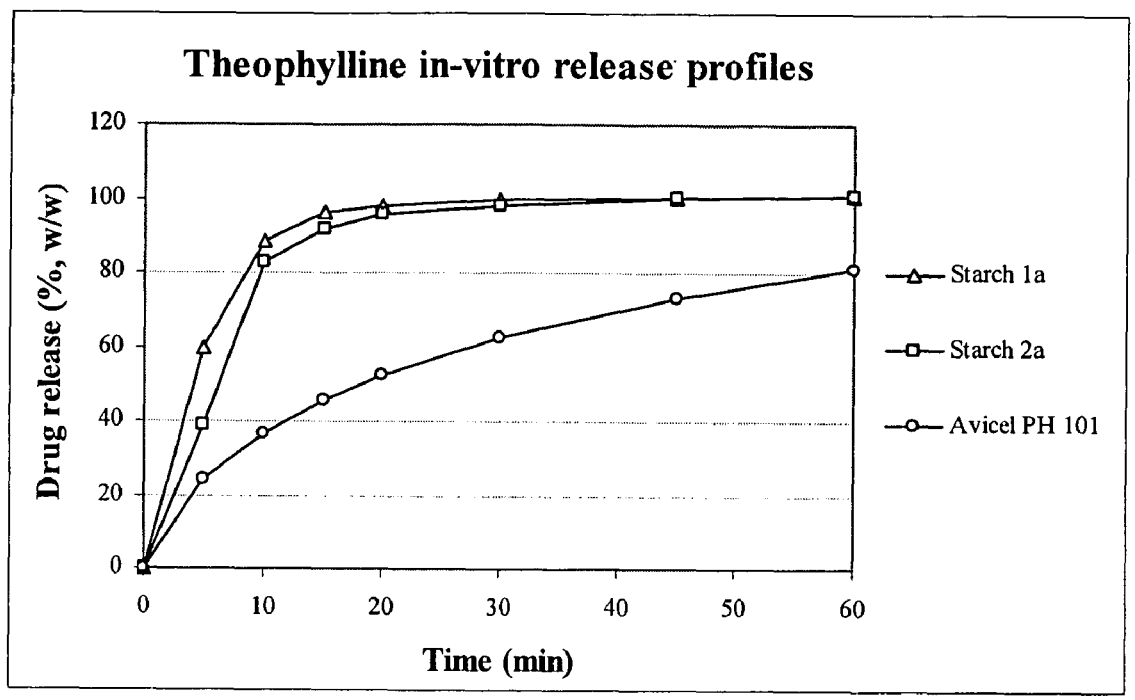
FIG. 1 depicts in vitro drug release profiles of pellets containing two starches of the present invention compared to microcrystalline cellulose.

This patent pertains to the use of crystalline debranched starch in the preparation of pharmaceutical pellets by extrusion-spheronization. Such excipients are useful in any dry dosage form, including tablets and capsules, for either immediate or sustained release.

Starch, as used herein, is intended to include all starches derived from any native source, any of which may be suitable for use herein. A native starch as used herein, is one as it is found in nature. Also suitable are starches derived from a plant obtained by standard breeding techniques including crossbreeding, translocation, inversion, transformation or any other method of gene or chromosome engineering to include variations thereof. In addition, starch derived from a plant grown from artificial mutations and variations of the above generic composition, which may be produced by known standard methods of mutation breeding, are also suitable herein.

Typical sources for the starches are cereals, tubers, roots, legumes and fruits. The native source can be varieties of corn (maize), pea, potato, sweet potato, banana, barley, wheat, rice, oat, sago, amaranth, tapioca (cassava), arrowroot, canna, and sorghum, as well as low amylose and high amylose varieties thereof. In one embodiment, the low amylose starch contains less than 5% amylose, in another embodiment less than 3%, and in yet another embodiment less than 1% amylose. In one embodiment, the high amylose starch contains containing at least 70%, in yet another embodiment at least 80%, and in a further embodiment, at least 90% amylose by weight of the dry starch. In one suitable embodiment, the starch is an amylose-containing starch and in another a high amylose starch with at least 70% amylose by weight.

The starting starch may be dispersed into an aqueous slurry and heated at sufficient temperature and pressure to effect gelatinization. Although gelatinization may be effected by any of the methods known in the art, the preferred method is to force the starch slurry through a jet cooker. Jet-cookers are well known in the industry and consist of a cooking chamber in which the starch slurry is contacted with live steam under elevated temperatures. In one embodiment, gelatinization is complete as determined visually by the total disintegration of granular structure. The gelatinization process disrupts, in whole or in part, the associative bonding of the starch molecules within the raw starch granule. This prepares the starch molecules for debranching by making them more accessible to the debranching enzyme, resulting in more uniformly debranched starch molecules.

After the starch has been gelatinized, it may then be prepared for enzymatic debranching by adjusting the starch solids content to the highest feasible solids level (to keep the amount of water low and to facilitate subsequent drying of the starch). A higher solids starch system may be employed if the starch is processed with adequate mixing to uniformly blend enzyme and starch at the higher solids.

Alternative methods of preparation for enzymatic debranching known in the art may be used. For example, gelatinization is not necessary if using an enzyme which is capable of acting on a granular starch. Another example is using the high solids, single phase process as disclosed in U.S. Pat. No. 6,054,302. Yet another alternative example is use of an enzyme immobilized on a solid support.

The temperature and pH of the starch may be adjusted to provide optimum enzyme activity. These parameters will vary depending upon the type and source of enzyme used, the enzyme concentration, the substrate concentration, and the presence or absence of inhibitors.

Any debranching enzymes (or blends of such enzymes) are suitable for use in this application. The enzymes useful in the present invention include without limitation endo-alpha-1,6-glucanohydrolases, such as pullulanase, isoamylase, or any other endo-enzyme that can cleave the 1,6-linkages of the starch molecule. In one embodiment, the enzyme not only cleaves the 1,6 linkages of the starch, but also leaves the 1,4-linkages substantially intact. In one embodiment, the enzyme used is pullulanase and in another embodiment, isoamylase.

The enzymatic hydrolysis of the starch base is carried out using techniques known in the art. The amount of enzyme used is dependent upon the enzyme, i.e., type, source and activity, and base material used as well as the amount of hydrolysis desired. In one embodiment, the enzyme is used in an amount of from about 0.01 to about 1.0%, and in another from about 0.01 to 0.3%, by weight of the starch.

The optimum parameters for enzyme activity will vary depending upon the enzyme used. The rate of enzyme degradation depends upon factors known in the art, including the type of enzyme used, enzyme concentration, substrate concentration, pH, temperature, the presence or absence of inhibitors, and the degree and type of modification. These parameters may be adjusted to optimize the digestion rate of the starch base.

In one embodiment, the enzyme used is pullulanase or pullulan 6-glucanohydrolase), a heat stable enzyme obtained from a species of Bacillus. Pullulanase will catalyze the hydrolysis of the alpha-1,6 linkages in amylopectin, provided that there are at least two glucose units in the side chain. At pH 5.0 the temperature for the aqueous starch dispersion during the enzymatic debranching by the Bacillus pullulanase will be between 25 and 75° C. If shorter treatment times are desired, the optimum temperature range should be at the upper portion of this range, from 60 to 75° C. (or even higher, if the debranching enzyme is thermally stable at the higher temperatures), or a higher enzyme concentration can be used.

As with other parameters of the enzyme reaction, the preferred and optimum temperature ranges will vary with changes in other parameters that affect enzyme activity, such as substrate concentration and pH, and these can be determined by the practitioner. Buffers, such as acetates, phosphates, citrates, or the salts of other weak acids may be added to ensure that the pH will be at the optimum level throughout the debranching. Optimum concentrations of enzyme and substrate are governed by the level of enzyme activity, which will vary depending upon the enzyme source, the enzyme supplier, and the concentration of the enzyme provided in commercially available batches.

The enzymatic treatment may be permitted to continue until the desired amount of debranching has occurred and in one embodiment, until essentially complete debranching has occurred; that is, no significant additional debranching will occur using that specific enzyme and other parameters. If desired, the progress of the debranching may be measured by any method known in the art for measuring the degree of enzymatic debranching of starch molecules. The enzyme reaction is continued until the starch is completely debranched. In general, the enzyme reaction will take from about 1 to about 24 hours, particularly about 4 to about 12 hours. The time of the reaction is dependent upon the type of starch used, the amount of enzyme used, and the reaction parameters of solids percent, pH, and temperature.

The amount of hydrolysis may be monitored and defined by measuring the concentration of reducing groups which are freed by alpha-1,6-D-glucanohydrolase activity by methods well known in the art. Other techniques such as monitoring the change in viscosity, iodine reaction, or the change in molecular weight may be used to define the reaction end point. When the starch is completely debranched, the monitored measurement will no longer change. Typically, the starch will be completely debranched when it has been at least about 95%, more particularly at least about 98%, most particularly at least about 99% debranched by weight. The debranched starch will typically have an average chain length of 14-25 glucose units and less than about 0.2%, particularly less than about 0.1% alpha-1,6-D-glucosidic bonds (linkages). Increased debranching will typically lead to a more crystalline starch product.

After the desired amount of starch debranching has been accomplished, the enzyme may be deactivated, for example by pH or heat. *Bacillus Pullulanase*, for example, is rapidly deactivated at temperatures above about 70° C.; therefore, the reaction using pullulanase may be conveniently terminated by increasing the temperature of the starch dispersion to at least 75° C. for about 15 minutes. Alternatively, the enzyme can be deactivated by adjusting the pH of the starch dispersion to below 3.0 and holding at that pH for about thirty minutes.

After debranching and deactivation of the enzyme, the starch is allowed to crystallize by methods known in the art, such as by retrogradation. This may be done by any method known in the art, and is conventionally done by allowing the starch to stand, and in one embodiment is done by allowing the starch to stand at temperatures below room temperature, such as at refrigerator temperatures.

The starch may be recovered using methods known in the art, particularly by extrusion, filtration, centrifugation, or drying, including spray drying, freeze drying, flash drying or air drying, more particularly by filtration or flash drying and in one particular embodiment is by extrusion or flash drying. The drying may be done to a partial extent, for example, to 60%-80% solids, and the resultant product then dried further. Alternatively, the starch can be dried to 100% solids, conventionally 10-15% moisture by weight of the dry starch. It is important to control the crystallization, typically by controlling retrogradation and drying, in order to obtain the necessary degree of crystallinity which is important to the present invention. It is further important that the method of drying and other post-crystallization processes do not substantially destroy the crystals.

The particle size of the dried powder may be adjusted using methods known in the art including, without limitation, by agglomeration. The particle size of the dried powder may be controlled during manufacture by methods known in the art to obtain an average (mean) particle size of, in one embodiment, at least about 25 microns, and no more than about 90 microns.

Optionally, the moisture content may be adjusted to allow for improved flow and compaction. Crystallization may be controlled using methods known in the art, such as by controlling retrogradation and drying, in order to obtain the desired degree of crystallinity. The starch must be at least partially crystalline in order to work in the spheronization process.

In another embodiment, the starch product is isolated by adding an inorganic salt to the starch dispersion and incubating the mixture at 50 to 100° C. The salt can be any known salt that will not interfere with starch retrogradation and that will act to help draw out the water of gelatinization, permitting the association of the linear starch molecules. Suitable salts include without limitation sodium sulfate, ammonium sulfate or magnesium sulfate, and sodium chloride. In one embodiment, the salts are added to the deactivated starch slurry in a minimum of 10% of the solids content.

The starches may also be converted and include without limitation fluidity or thin-boiling starches prepared by oxidation, acid hydrolysis, and enzyme hydrolysis. These processes are well known in the art and may be accomplished either before or after debranching.

The starch may also be further modified, either before or after the enzymatic hydrolysis. Such modification may be physical, enzyme, or chemical modification. Physical modification includes by shearing or thermally inhibiting, for example by the process described in U.S. Pat. No. 5,725,676.

Chemical modification includes without limitation, crosslinking, acetylation and organic esterification, hydroxyalkylation, phosphorylation and inorganic esterification, cationic, anionic, nonionic, and zwitterionic modifications, and succination. Such modifications are known in the art, for example in *Modified Starches: Properties and Uses*, Ed. Wurzburg, CRC Press, Inc., Florida (1986).

Any starch base having suitable properties for use herein may be purified by any method known in the art to remove starch off flavors and colors that are native to the polysaccharide or created during processing. Suitable purification processes for treating starches are disclosed in the art and include without limitation alkali washing techniques. Such purification methods are also useful on the debranched starch.

If purification of the debranched starch composition is desired, reaction impurities and by-products may be removed by dialysis, filtration, centrifugation or any other method known in the art for isolating and concentrating starch compositions. For example, the degraded starch may be washed using techniques known in the art to remove soluble low molecular weight fractions, such as oligosaccharides, resulting in more highly crystalline starch. In one embodiment, a narrow range of molecular weights is isolated and allowed to crystallize, to result in a more crystalline starch.

The resultant solution is typically adjusted to the desired pH according to its intended end use. In general, the pH is adjusted to from about 5.0 to about 7.5, and in one embodiment from about 6.0 to about 7.0, using techniques known in the art. Further, any short chain amylose which precipitated out of the starch dispersion may be redispersed or removed.

The starch is uniquely functional as a pharmaceutical excipient for use in extrusion-spheronization. The process is based on the following steps:

a) the mixing of one or more debranched starches, and optionally other excipients and/or one or more active agents, to obtain a uniform mixture in form of dry powder to which a suitable amount of liquid is added to obtain a moistened plastically deformable mass;

b) the extrusion of the mixture obtained from the step a) through a perforated mesh in order to obtain cylindrical extrudates having desired length and diameter;

c) the spheronization of the extrudates in order to obtain a product in the form of spherical pellets;

d) the drying of the pellets;

e) the optional depositing of at least one active agent on the surface of the pellets; and f) the optional coating of the pellets.

The starch may be used as the sole excipient or in combination with microcrystalline cellulose and/or other cellulose derivatives. In one embodiment, the debranched starch is used in an amount of at 10-100%, in another embodiment at 25-95%, and in a third embodiment at 60-90%, by weight of the plastically deformable mass on a dry basis. In another embodiment, the debranched starch is used as the primary excipient (greater than 50% of the excipients by weight) and is used in combination with a binder, the binder being present in an amount of up to 8% by weight of the plastically deformable mass on a dry basis.

In one embodiment, binders are added to the formulation in an amount of up to about 25%, and in another embodiment in an amount of up to about 15%, and in yet another embodiment in an amount of up to about 8%, all by weight of the plastically deformable mass on a dry weight basis to help the material withstand the frictional forces of spheronization and result in a larger pellet size. In one embodiment, the binder is present in an amount of from 4-8% by weight of the plastically deformable mass on a dry weight. Binders include those commonly known in the art and in one embodiment is selected from the group consisting of hydroxypropyl methylcellulose, drum dried waxy corn starch, hydroxypropyl cellulose and polyvinylpyrrolidone and in another from hydroxypropyl methyl cellulose and drum dried waxy corn starch.

Optionally, a plasticizer may be added to improve the surface properties of the pellets and in one embodiment is added in an amount of up to 30%, in one embodiment in an amount of up to 25%, and in another up to 15%, by weight plastically deformable mass on a dry basis. In one aspect of the invention, the plasticizer is a polyol and in another is sorbitol.

The liquid added to form a moistened mass for extrusion may include any liquid substance or mix (solution or emulsion) of liquids of normal pharmaceutical use able to moisten the powder mix, as for example water, aqueous solutions having different pH, organic solvents of normal pharmaceutical use (for example, alcohols, chlorinated solvents, and oils). In one embodiment, the liquid is water. The wet mass may be prepared using any equipment known in the art including without limitation a planetary mixer, high-shear mixer, sigma blade mixer, or continuous granulator.

The liquid is added in any desirable amount and in one aspect of the invention is added in an amount of from 20 to 55% and in another aspect from 30 to 45% based on the wet weight of the plastically deformable mass.

In one aspect of the invention, the active agent and/or excipients may be dissolved, dispersed and/or emulsified in such liquids.

The moistened mass is extruded through a perforated mesh in order to produce extrudates (cylindrical filaments). The port of the meshes determines the diameter of the extrudates and in one embodiment is from about 0.2 mm to 3 mm and in another from about 0.5 mm to about 2 mm. The extrusion may be carried out using single screw, double screw, "sieve and basket" kind, "roll extruder", "ram extruder" extruders or any other pharmaceutically acceptable means to produce extrudates. In one embodiment of this invention a double screw coaxial extruder may be used.

In one aspect of the invention, the extruded mass may be re-extruded prior to spheronization in order to obtain a higher densification level of the extrudates.

The extrudates obtained by extrusion are then spheronized. The spheronization device consists of a hollow cylinder with a horizontal rotating plate. The extrudates are broken in short segments which are transformed to pellets on the upper surface of a rotating plate, and in one aspect of the invention at a velocity ranging from about 200 rpm to about 2,000 rpm. The pellets may be dried in any pharmaceutically acceptable way, such as drying at room temperature and may be accomplished in any apparatus known in the art including without limitation, in an oven, a fluidized bed, or a microwave oven.

Use of debranched starches provides a yield of greater than 80% and in one embodiment greater than 90%. Yield is intended to mean the percent of the extruded composition which resulted in usable pellets, that is pellets which are substantially spherical solid particles whose diameter size range from about 100 microns to about 3 mm. In one embodiment, the diameter of the pellets ranges from about 0.70 to 1.40 mm. Fines and pellets which are not of the desired size may be removed from the resultant pellets by techniques known in the art, such as sieving.

In one embodiment, the pellets had an aspect ratio of between 1.1 and 1.2. In one embodiment, the pellet friability was less than 2% and in another aspect less than 0.5%. Pellets exhibited immediate disintegration in aqueous medium and substantially immediate disintegration in artificial gastric and intestinal fluids.

The pellets may be used as they are or may be coated. In one embodiment, the coating is with an active agent, either the same as or different from the active agent, if any, within the pellet. In another embodiment, the pellets are coated for functional purposes, which include without limitation to obtain a controlled release effect, to mask the taste, to improve the shelf-life, and for identification purposes. The optional coating may contain an active agent as well as at least one functional ingredient. The pellets may be used in tablets, capsules, packets and other formulations.

A variety of starch compatible active agents may be employed in this invention. The particular nature of the active ingredient is not critical, and pharmaceutical and non-pharmaceutical active ingredients, such as nutritional supplements, detergents, dyes, pesticides, agricultural chemicals, enzymes, and foods may also be employed. Typical products include without limitation capsules and tablets not only for pharmaceutical uses, but also for detergents, fertilizers, pesticides, animal feed pellets, food and non-food uses.

Pharmaceutically active agents means any physiologically or pharmacologically acceptable substance, organic or inorganic, of natural or synthetic origin, producing systemic or local effects in living beings. The active principles which may be vehiculated by the pellets of this invention include without limitation drugs acting on the central nervous system and on the peripheral nervous system, cardiovasculars, hypotensives, diuretics, anti-inflammatories, analgesics, antifebriles, antiasthmatics, bronchodilatators, antitussis, mucolytics, antibiotics, chemotherapeutic agents, antivirals, hormones, antineoplastics, immunosuppressants, immunostimulants, peptides, polypeptides, proteins, vaccines, antiarrhythmics, antifungals and antipsoriatics, antivirals, antihypertensives, antidepressants, antihistaminics, antineoplastics and immunosuppressants, anxiolytics, sedatives, hypnotics, beta-blockers, beta-agonists, cardiac and cardiovascolar inotropics, corticosteroids, gastrointestinals and anti H2-histaminics, hypolipidemics, anti-anginals, central action drugs. vitaminic and nutritional agents, opioid analgesics, sexual hormones, and peptidic, proteic or polysaccharidic molecules.

The active agents may be distributed inside the pellets and/or they may be deposited on the surface of the pellets by techniques normally used in the pharmaceutical arts, including without limitation by spray drying and coating.

In the case that an active principle is distributed inside the microparticles, it ranges from about 0.1% to about 95% by weight of the microparticles.

Additional pharmaceutical excipients known in the art may be added to the pharmaceutical dosage form to impart satisfactory processing, disintegration, or other characteristics to the formulation. Such excipients include, but are not limited to, flow enhancers, surfactants, lubricants and glidants, disintegrants, colors, flavors and sweetening agents. These excipients are well known in the art and are limited only by compatibility and characteristics desired.

Lubricants and glidants include talc, magnesium stearate, calcium stearate, stearic acid, glyceryl behenate, mineral oil, polyethylene glycol, sodium stearyl fumarate, stearic acid, vegetable oil, zinc stearate, and silicon dioxide.

Disintegrants suitable for the present invention include starches, algins, gums, croscarmelose, crospovidone, sodium starch glycolate, sodium lauryl sulfate, microcrystalline cellulose, polacrilin potassium, and methylcellulose.

If the final desired product is other than a pharmaceutical dosage form, alternative additives known to those arts may be present. For example, flavors and fragrances in a bath oil tablet or surfactants in a detergent tablet.

Other methods of granulation known in the art which involve high shear may be used to form the pellets including fluid-bed and rotogranulation, centrifugal granulator, or high-shear granulation.

EXAMPLES

The following examples are presented to further illustrate and explain the present invention and should not be taken as limiting in any regard. All percents used are on a weight/weight basis.

The following test procedures are used throughout the examples:

Aspect ratio—Image analysis was used to determine the aspect ratio of each individual pellet. The result represents the mean aspect ratio value of around 300 pellets.

Friability—Friability value is expressed as the % weight loss of the pellet mass (initially around 10 g), after 250 rotations during 10 minutes in a friabilator. To increase the mechanical stress on the pellets, 200 glass beads (4 mm in diameter) were added to the pellets.

In-vitro dissolution rate—To test drug release from the pellets, USP XXVII dissolution test (apparatus 2, paddle rotational speed: 50 rpm) was used. The amount of sample tested was 300 mg (according to the "sink conditions" for theophylline with solubility of 8.3 mg/mL) in 900 mL of water as a dissolution medium. Detection was performed by means of UV-spectrophotometer at 272 nm (max absorption wave length for theophylline).

Example 1

Preparation of the Debranched Starch Using Pullulanase and High Amylose Corn Starch a. HYLON® VII starch, a high amylose corn starch commercially available from National Starch and Chemical Company (Bridgewater, N.J.) was slurried into water and jet cooked at temperatures between 149-160° C. to fully gelatinize the starch. The starch cook was then held at a constant set temperature of 60° C. The starch dispersion was diluted to a solids range of 10% to 20%. The pH was adjusted to about 5.0, with a solution of 3:1 water/concentrated HCl. Promozyme 400 L, a commercial preparation of pullulanase, a product of NOVOZYMES, Danbury Conn., was added when the starch temperature was about 60° C. and the enzyme was allowed to debranch the starch for 48 hours, and then was heat deactivated by raising the temperature at which point the solution was allowed to anneal. The starch was then neutralized to a pH of 5.0-5.5 with 3% NaOH in water. The debranched starch was then isolated by spray drying.

b. Example 1a was repeated except the debranched starch was dried by extrusion. Extrusion was conducted on a Warner & Pfleiderer Type ZSK-30 twin-screw extruder. The screw configuration used is designated 12-44 and was used with a 5 mm$^2$ die. The screws were operated at a speed of 400-450 rpm and the barrel heating zones were set to 60° C./100° C./120° C./150° C./150° C. The barrel was placed under a vacuum of 35-40 cm Hg (14-16 inches Hg) through a single barrel vent.

c. Example 1a was repeated except the debranched starch was isolated by centrifugation using a perforated bowl centrifuge with a linen cloth as the filter medium.

d. Example 1c was repeated and then flash dried using a laboratory flash dryer having an inlet temperature of 250° C. and an outlet temperature of 175° C. at a feed rate of 7.0 g/min.

e. Example 1a was repeated except that the HYLON® VII starch was modified with 1.25% octenyl succinic anhydride before cooking using the following conditions: HYLON VII starch (800 g) was slurried into 1200 ml of water. The pH of the slurry was raised to 7.4 with 3% NaOH. While maintaining the pH at 7.3-7.4, three increments of octenyl succinic acid anhydride, 3.3 ml each, were added with agitation ½ hour apart. When the reaction no longer consumed caustic, it was determined to be complete and the starch was collected by filtration.

g. Example 1a was repeated except prior to filtering, food grade salts were added to the debranched starch (in separate samples, 10% or 25% ammonium sulfate, 25% magnesium sulfate, and 25% or 50% sodium chloride based on percent starch solids). Each of these mixtures was heated to 95° C. and held at that temperature for 24 hours. The sample was cooled to about 25° C. and ethanol was added to bring the solvent to a solution of 50:50 ethanol:water and to precipitate out the starch product. The product was filtered over a Buchner funnel, washed twice with 50:50 water:ethanol and air dried.

h. Example 1a was repeated except the enzyme was pH deactivated by lowering the pH to about 3.0 with a solution of 3:1 water:concentrated HCl for 30 minutes.

i. HYLON® VII starch, a high amylose corn starch commercially available from National Starch and Chemical Company (Bridgewater, N.J.) was slurried into water at around 20% solids and the pH is adjusted to around 4.0 with 3% NaOH and jet cooked at temperatures between 160-166° C. to fully gelatinize the starch. The solution of cooked starch is cooled to around 55° C. and then isoamylase a commercial debranching enzyme obtained from Hayashibara (Japan) and the starch was allowed to debranch for 18 hours while maintaining the temperature at 55 C. The pH was adjusted as needed to around 5.0 with 3% NaOH. The temperature was then raised to around 91-96 C. in order to deactivate the enzyme and allow for annealing of the starch. The starch was then cooled to around 55 C. and the starch was isolated as a powder using spray drying.

Example 2

Preparation of the Debranched Starch Products Using Isoamylase Debranched Waxy Maize Starch a. Two kilograms of acid converted waxy maize starch was slurried in 5.4 liters of water. The pH of the slurry was adjusted to 4.0 by adding 3:1 water:hydrochloric acid (HCl). The slurry was jet-cooked with full steam at 310-315° F. (154.4-157.2° C.) and 80 psi (5.52×10$^5$ Pa) back-pressure. The cooked starch solution was put into a reaction container in a 55° C. water bath. 0.2% (wu wt) isoamylase (commercially available from Hayashibara Inc. Japan) based on starch was added to start the debranching reaction. Reaction conditions were maintained at 55° C. and pH 4.0 during the entire reaction.

After the reaction proceeded for 5 hours, the pH was adjusted to 5.5 using a 3% solution of sodium hydroxide. The isoamylase enzyme was then denatured by heating the sample to 85-90° C. in a boiling water bath for 20 minutes. The sample was cooled to room temperature and agitated at room temperature (25° C.) overnight (16 hours). The product was filtered to produce a starch cake and air-dried. The product had a degree of polymerization (DP) of 15 using Nelson/Somogyi reducing sugar test and gave a type-B x-ray diffraction pattern.

b. The method of Example 1A was repeated with the exception that the sample was cooled to 40° C. and held at 40° C. overnight for the crystallization instead of at room temperature. The product gave a type-A x-ray diffraction pattern.

c. The method of Example 1A was repeated with the exception that the sample was crystallized at 4° C.

d. The method of Example 1A was repeated with the exception that the reaction time was allowed to proceed for 24 hours instead of 5 hours. The product had a D.P. of 14 and gave a type-A x-ray diffraction pattern.

Example 3

Preparation of Debranched Starch Product Using Low Solid Reaction 1.8 kg of waxy maize starch was slurried in 5.4 liter of water. The sample was jet-cooked with full steam at 310-315° F. (154.4-157.2° C.) and 80 psi ($5.52 \times 10^5$ Pa) backpressure. The cooked starch solution was diluted to 10% solid and put into a reaction container at 55° C. The sample pH was adjusted to 4.0 by adding 3:1 water:HCl. The sample temperature was maintained at 55° C. and 0.2% isoamylase was added to start the debranching reaction. After sample DE reached 7.5 (about 8 hours), the pH was decreased to 2.0 for 30 minutes to denature the enzyme, and then increased to 6.0 using 3% sodium hydroxide. The sample was cooled to room temperature and allowed to crystallized overnight (16 hours). A sample cake was obtained by filtration and the sample was air-dried.

Example 4

Extrusion Spheronization Using Debranched Starches a. A dry blend of 62.5 g (25%, dry mass) of anhydrous theophylline (Eur. Ph.), 15.0 g (6%, dry mass) of hydroxypropylmethylcellulose (Methocel® E15 Premium LV EP) and 172.5 g (69%, dry mass) of the starch of Example 1a was wet massed with 200.0 g (44.4%, wet mass) of water in a planetary mixer for 10 minutes. Wet mass was then extruded by means of dome screw extruder through extrusion screen with 1 mm die opening and the extrusion speed of 50 rpm. Extruded wet mass was then spheronised at speed of 850 rpm for 2 minutes and 30 seconds. Obtained wet pellets were dried in a fluidized bed at inlet air temperature of 60° C. for around 40 minutes, until the constant weight of the material was obtained.

Dry pellets were sieved and the yield of 86.1% was obtained.

The aspect ratio was 1.14.

Friability was 0.25%. The drug release profile is described as follows:
60% of theophylline was released after 5 minutes;
89% of theophylline was released after 10 minutes;
96% of theophylline was released after 15 minutes;
98% of theophylline was released after 20 minutes; and
100% of theophylline was released after 30 minutes.

Pellets disintegrated 15 minutes after they were immersed into dissolution medium.

b. A dry blend of 62.5 g (25%, dry mass) of anhydrous theophylline (Eur. Ph.), 11.25 g (4.5%, dry mass) of hydroxypropylmethylcellulose (Methocel® E15 Premium LV EP), 28.125 g (11.25%, dry mass) of sorbitol and 148.25 g (59.25%, dry mass) of the starch of Example 1a was wet massed with 148 g (37%, wet mass) of water in a planetary mixer for 10 minutes. Pellets were obtained as described in Example 4a.

Dry pellets were sieved and the yield of 87.4% was obtained.

The aspect ratio was 1.12.

Friability was 0.02%. The drug release profile is described as follows:
40% of theophylline was released after 5 minutes;
76% of theophylline was released after 10 minutes;
93% of theophylline was released after 15 minutes;
99% of theophylline was released after 20 minutes; and
100% of theophylline was released after 30 minutes.

Pellets disintegrated 10 minutes after they were immersed into dissolution medium.

c. A dry blend of 17.5 g (7%, dry mass) of hydroxypropylmethylcellulose (Methocel® E15 Premium LV EP), 25 g (10%, dry mass) of sorbitol and 207.5 g (83%, dry mass) of the starch of Example 1e was wet massed with 142 g (36.2%, wet mass) of water in a planetary mixer for 10 minutes. Wet mass was then extruded by means of a dome screw extruder through an extrusion screen with 1 mm die opening and an extrusion speed of 60 rpm. Extruded wet mass was then spheronised at a speed of 850 rpm for 3 minutes. The wet pellets obtained were dried in an oven at 40° C., until the constant weight of the material was obtained.

Dry pellets were sieved and a yield of 94.8% was obtained.

The aspect ratio was 1.14.

Example 5

Comparison with Other Starches and Blends a. A dry blend of 62.5 g (25%, dry mass) of anhydrous theophylline (Eur. Ph.), 3.75 g (1.5%, dry mass) of hydrohypropylmethylcellulose (Methocel® E15 Premium LV EP) and 183.75 g (73.5%, dry mass) of the starch of Example 2a was wet massed with 125.0 g (33.3%, wet mass) of water in a planetary mixer for 10 minutes. Wet mass was then extruded by means of dome screw extruder through extrusion screen with 1 mm die opening and the extrusion speed of 70 rpm. Extruded wet mass was then spheronised at speed of 850 rpm for 3 minutes. Obtained wet pellets were dried in an oven at 40° C. for around 30 hours, until the constant weight of the material was obtained.

Dry pellets were sieved and the yield of 73.6% was obtained.

The aspect ratio was 1.13.

Friability was 0.14%.

The drug release profile is described as follows:
40% of theophylline was released after 5 minutes;
83% of theophylline was released after 10 minutes;
92% of theophylline was released after 15 minutes;
96% of theophylline was released after 20 minutes;
98% of theophylline was released after 30 minutes; and
100% of theophylline was released after 45 minutes.

Pellets disintegrated 30 minutes after they were immersed into dissolution medium.

b. A dry blend of 62.5 g (25%, dry mass) of anhydrous theophylline (Eur. Ph.) and 187.5 g (75%, dry mass) of microcrystalline cellulose (Avicel® PH 101) was wet massed with 237.5 g (48.7%, wet mass) of water in a planetary mixer for 5 minutes. Wet mass was then extruded by means of dome screw extruder through extrusion screen with 1 mm die opening and the extrusion speed of 50 rpm. Extruded wet mass was then spheronised at speed of 850 rpm for 2 minutes and 30 seconds. Obtained wet pellets were dried in a fluidized bed at inlet air temperature of 60° C. for around 40 minutes, until the constant weight of the material was obtained.

Friability was 0.22%.

The drug release profile is described as follows:
24% of theophylline was released after 5 minutes;
37% of theophylline was released after 10 minutes;
45% of theophylline was released after 15 minutes;
52% of theophylline was released after 20 minutes;
62% of theophylline was released after 30 minutes;
73% of theophylline was released after 45 minutes; and
81% of theophylline was released after 60 minutes.
Pellets did not disintegrate during dissolution testing.

c. A highly degraded, amorphous, 70% amylose corn starch was tried in the spheronisation process, but could not be processed as the addition of water produced a sticky, chewing gum like mass.

d. An amorphous, short chain amylose starch prepared by debranching waxy corn starch was tried in the spheronisation process, but could not be processed as the addition of water produced a sticky, chewing gum like mass.

Example 6

Crystallization of Samples by X-Ray Powder Diffractometry

Figure 2:
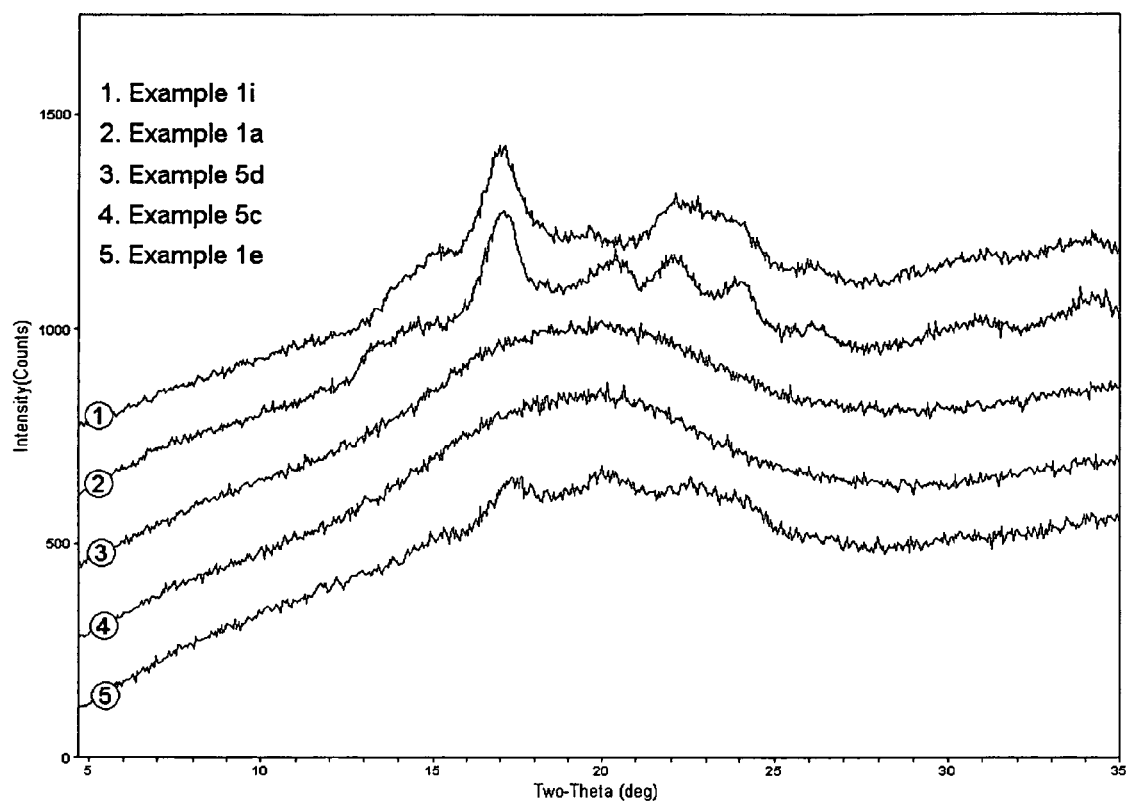
FIG. 2 depicts x-ray diffraction spectra of starch examples.

X-Ray diffraction spectra were collected of starch samples using Rigaku Miniflex X-ray diffractometer in continuous scan mode, with variable divergence slits, in the 2 theta/theta range from 5 to 35 degrees (sampling frequency 0.020 deg) using Cu Kalpha radiation (0.154 nm) at 30 kV. The results, depicted in FIG. 2, show that Samples 1, 2, and 5 are crystalline.

Sample 1 (starch of Example 1 i) and Sample 2 (starch of Example 1a) both showed a diffraction pattern typical for type B crystalline structure. Sample 3 (starch of Example 5d) and sample 4 (starch of Example 5c) both exhibited a broad curve typical of amorphous starches with a maximum at around 20 deg. 2 theta. The last sample (starch of Example 1e) showed shallow peaks, typical for a starch with a small degree of crystallinity.

We claim:

1. A process comprising the steps of:
    a) mixing at least one crystalline debranched high amylose starch and water to form a moistened plastically deformable mass, wherein the mass comprises greater than 50%, by weight on a dry basis, of the starch;
    b) extruding the mass to obtain an extrudate;
    c) spheronizing of the extrudate to obtain a plurality of substantially spherical pellets; and
    d) drying of the pellets;
    wherein the starch has an amylose content of at least 70% by weight.

2. The process of claim 1, wherein at least one excipient is mixed in with the starch and water of step (a).

3. The process of claim 1, wherein at least one active agent is mixed in with the starch and water of step (a).

4. The process of claim 1, further comprising depositing at least one active agent on the surface of the pellets.

5. The process of claim 1, further comprising coating at least one active agent and/or functional ingredient on the surface of the pellets.

6. The process of claim 5, wherein the functional ingredient provides a function to the pellets selected from the group consisting of controlled release, taste masking, improved shelf-life, and identification.

7. The process of claim 1, wherein the starch is debranched using pullulanase or isoamylase.

8. The process of claim 1, wherein the starch is a corn starch.

9. The process of claim 2, wherein the starch is present in an amount of 10-100% by weight of the plastically deformable mass on a dry basis.

10. The process of claim 2, wherein the excipient is a binder present in an amount of up to 15% by weight of the plastically deformable mass on a dry weight basis.

11. The process of claim 10, wherein the binder is selected from the group consisting of hydroxypropyl methylcellulose, drum dried waxy corn starch, hydroxypropyl cellulose and polyvinylpyrrolidone.

12. The process of claim 11, wherein the binder is selected from the group consisting of hydroxypropyl methyl cellulose and drum dried waxy corn starch.

13. The process of claim 2, wherein the at least one excipient is a plasticizer in an amount of up to 30% by weight plastically deformable mass on a dry basis.

14. The process of claim 13, wherein the plasticizer is a polyol.

15. The process of claim 14, wherein the polyol is sorbitol.

16. The process of claim 1, wherein the water is in an amount of from 20 to 55% based on the wet weight of the plastically deformable mass.

17. The process of claim 1, further comprising re-extruding the extrudate.

18. The process of claim 1, wherein greater than 80% of the pellets have a diameter of from about 0.70 to 1.40 mm.

19. The process of claim 3 wherein the active agent is selected from the group consisting of pharmaceuticals, nutritional supplements, detergents, dyes, pesticides, agricultural chemicals, enzymes, and foods.

20. The process of claim 3, wherein the active agent is a pharmaceutical.

21. The process of claim 4, wherein the active agent is selected from the group consisting of pharmaceuticals, nutritional supplements, detergents, dyes, pesticides, agricultural chemicals, enzymes, and foods.

22. The process of claim 5, wherein the active agent is selected from the group consisting of pharmaceuticals, nutritional supplements, detergents, dyes, pesticides, agricultural chemicals, enzymes, and foods.

23. The process of claim 4, wherein the active agent is a pharmaceutical.

24. The process of claim 5, wherein the active agent is a pharmaceutical.

* * * * *